United States Patent [19]

Reemtsma et al.

[11] Patent Number: 4,861,704
[45] Date of Patent: Aug. 29, 1989

[54] PROCESSES FOR DEVELOPMENT OF ACCEPTANCE OF TRANSPLANTED ORGANS AND TISSUES

[75] Inventors: Keith Reemtsma, New York; Mark A. Hardy, Scarsdale; Henry T. Lau, New York, all of N.Y.

[73] Assignee: The Trustees of Columbia University in the City of New York, New York, N.Y.

[21] Appl. No.: 918,282

[22] Filed: Oct. 8, 1986

Related U.S. Application Data

[63] Continuation of Ser. No. 528,525, Sep. 1, 1983, abandoned.

[51] Int. Cl.$^4$ .................. A01N 1/02; C12N 13/00
[52] U.S. Cl. ................................ 435/1; 435/173; 128/395; 604/49
[58] Field of Search ................. 435/1, 2, 173, 283; 424/95, 101; 128/395; 604/4, 20, 49, 52, 905; 204/157.15, 158.21

[56] References Cited

U.S. PATENT DOCUMENTS

| | | | |
|---|---|---|---|
| 1,683,877 | 9/1928 | Edslam et al. | 604/4 X |
| 3,973,001 | 8/1976 | Jaeger et al. | 424/177 X |
| 4,321,918 | 3/1982 | Clark, II | 604/4 |
| 4,321,919 | 3/1982 | Edelson | 604/20 X |
| 4,428,744 | 1/1984 | Edelson | 604/20 X |
| 4,456,589 | 6/1984 | Holman et al. | 424/95 |
| 4,471,629 | 9/1984 | Toledo-Pereyra | 435/1 X |
| 4,608,255 | 8/1986 | Kahn et al. | 424/101 |

FOREIGN PATENT DOCUMENTS

| | | | |
|---|---|---|---|
| 2803446 | 8/1979 | Fed. Rep. of Germany | 604/20 |
| 3109691 | 9/1982 | Fed. Rep. of Germany | 604/4 |
| 0342630 | 7/1972 | U.S.S.R. | 424/101 |

OTHER PUBLICATIONS

Kimber et al., Anatomy and Physiology, New York, Macmillan, 1961, pp. 306–315, 430–431.
Spellman et al., Journal of Clinical Immunology, vol. 3, No. 2, Apr. 1983, pp. 105–110.
Greene et al., Proc. Nat. Acad. Sci., USA, vol. 76, No. 12, Dec. 1979, pp. 6591–6595.
Hardy et al., Transplantation, vol. 33, No. 3, 1982, pp. 237–242.
Reemtsma et al., Transplanation Proceedings, vol. 13, No. 1, Mar. 1981, pp. 801–806.
Hardy et al., Surgery, vol. 86, No. 2, Aug. 1979, pp. 194–202.
Iga et al., Eur. Surg. Res., 16 (Suppl. 1), 1984, p. 84.
Oluwole et al., Transplantation, vol. 28, No. 6, 1979, pp. 492–495.
Hardy et al., World Journal of Surgery, vol. 8, No. 2, Mar. 1984, pp. 207–213.
Hardy et al., Transplantation Proceedings, vol. 16, No. 3, Jun. 1984, pp. 865–869.
Lau et al., Science, vol. 221, Aug. 19, 1983, pp. 754–756.
Lau et al., Science, vol. 223, Feb. 10, 1984, pp. 607–609.
Hardy et al., Annals of Surgery, vol. 200, No. 4, Oct. 1984, pp. 441–450.
Lau et al., Transplantation, vol. 38, No. 6, 1984, pp. 566–569.
Hardy et al., Transplantation Proceedings, vol. 17, No. 1, Feb., 1985, pp. 423–424.
McGraw-Hill Yearbook of Science and Technology, New York, McGraw Hill, 1981, pp. 306–309.
Lau et al., Reprinted from American College of Surgeons 1983 Surgical Forum vol. XXXIV, pp. 367–369.

*Primary Examiner*—Robert J. Warden
*Assistant Examiner*—Randall E. Deck
*Attorney, Agent, or Firm*—John P. White

[57] ABSTRACT

A patient's acceptance of a transplanted organ or tissue from a donor may be enhanced by irradiating donor-specific blood with ultraviolet-B radiation at a dosage of less than 1000 J/M$^2$ so as to render the blood capable of inducing donor-specific immunological unresponsiveness in the patient, transfusing the irradiated, donor-specific blood into the patient prior to transplanting the organ or tissue into the patient to enhance subsequent acceptance of the organ or tissue by the patient, and thereafter transplanting the organ or tissue into the subject.

A patient's acceptance of transplanted organs and tissues can also be enhanced by removing the organ or tissue from the donor and irradiating the organ or tissue to be transplanted with ultraviolet-B radiation at a dosage of less than 1000 J/m$^2$ so as to enhance acceptance of the transplanted organ or tissue and then transplanting the irradiated organ or tissue into patient.

5 Claims, 4 Drawing Sheets

PROCESSES FOR DEVELOPMENT OF ACCEPTANCE OF TRANSPLANTED ORGANS AND TISSUES

The invention described herein was made in the course of work under grant numbers HL 14799 and AM 30468 from the National Institute of Health, United States Department of Health and Human Services, U.S.A.

This is a continuation of application Ser. No. 528,525 filed Sept. 1, 1983 now abandoned.

SUMMARY OF THE INVENTION

The acceptance of transplanted organs or tissues in a subject may be enhanced by treating donor specific blood with a suitable dose of ultraviolet radiation for an appropriate period of time, transfusing the irradiated blood into the subject during a suitable period of time prior to transplanting the organs or tissues and then transplanting the organs or tissues into the subject.

The acceptance of transplanted organs or tissues in a subject may also be enhanced by treating the organs or tissues to be transplanted with a suitable dose of ultraviolet radiation for an appropriate period of time and then transplanting the organs or tissues into the subject.

Suitably irradiated donor specific blood, organs and tissues are preferred for use in surgical transplantation.

BRIEF DESCRIPTION OF THE FIGURES

FIG. 2. The effect of dose of UV irradiation on the MLC stimulatory activity of Lewis dendritic cells (DC). MLC was performed using ACI thoracic duct lymphocytes (TDL) as responders and Lewis rat afferent lymph derived DC as stimulators. Methods used for isolation of dendritic cells have been previously described (20). In brief, abdominal lymph nodes were removed from rats six weeks prior to thoracic duct drainage. Lymph was collected over a 36 hour period and resultant cells were enriched for DC by a high density BSA centrifugation step (44). Resultant light density cells had a population of approximately 70% DC with their distinct morphological appearance (45). These cells were gamma irradiated (1600 rad) prior to UV irradiation and their use in MLC. DC were UV irradiated in open petri dishes while suspended under HBSS with constant stirring with a magnetic bar. Source of UV irradiation was a bank of two FS20 lamps which have a flux of 1mW/cm$^2$ at 310 nm, (UVX-Radiometer, UV Product, Calif.) measured 10 cm from source. Cells were cultured in triplicate in 96 well microtiter plates in RPMI 1640 containing 100 mg/ml streptomycin and penicillin and supplemented with 10% rat serum. Results represent (H$^3$)=thymidine incorporation after 96 hours of culture including a 16 hour (H$^3$) thymidine pulse period and are expressed as:

$$\text{Stimulation Index (SI)} = \frac{\text{experimental mean CPM}}{\text{control mean CPM}}$$

FIG. 3. Effect of dose of UV irradiation on islet function after syngeneic transplantation. Lewis rats were made diabetic with i.v. streptozotocin (60 mg/kg) (courtesy of Dr. Dulin, Upjohn, Kalamazoo, Mich.) and used as recipients if blood glucose was 300 mg/dl on three weekly successive measuremens. Lewis islets were isolated using collagenase digestion (46), Ficoll gradient separation (47) and subsequent hand-picking under a stereomicroscope. Isolated islets were suspended in HBSS in petri dishes and irradiated with constant stirring with a magnetic bar. UV source was same as described for DC irradiation. After irradiation, islets were placed into culture at 37° C., 5% $CO_2$ in CMRL 1066 with 10% FCS for 24 hours and transplanted via the portal vein. Group I islets received 80 J/m$^2$ (n=2); Group II islets received 900 J/m$^2$ (n=2); Group III islets received 1000 J/m$^2$ (n=2); and Group IV islets received 1100 J/m$^2$ (n=3). Stippled line represents normal blood glucose range.

DETAILED DESCRIPTION OF THE INVENTION

Throughout this application references are made using arabic numerals to various publications and explanatory matter set forth immediately preceding the claims under the heading "References and Notes." The entire disclosures of these references are hereby incorporated by reference into the present application to provide information concerning the state of the art as of the time the invention was made.

This invention provides a method for enhancing acceptance of transplanted organs or tissues in a subject which comprises treating donor specific blood with a suitable dose of ultraviolet radiation for an appropriate period of time, transfusing the irradiated blood into the subject during a suitable period of time prior to transplanting the organs or tissues into the subject and then transplanting the organs or tissues into the subject.

Although applicable to a wide variety of subjects the invention is primarily intended for use with human patients requiring an organ or tissue transplant. In principle the method may be used with any organ or tissue. Examples of such organs include the kidney, heart, lung, liver and intestine. Tissues may be derived from these organs or may be derived from other body tissues, e.g., bone marrow.

Varying doses of ultraviolet radiation may be employed to irradiate the organ or tissue to be transplanted. The presently preferred dosage is a dose less than about 1000 J/m$^2$. The organ or tissue may be exposed to the ultraviolet radiation for various periods of time. The presently preferred time for exposure to the ultraviolet radiation is a time period greater than about ten minutes, e.g., about twenty minutes.

The irradiated blood is desirably transfused into the subject into whom the organ or tissue is to be transplanted during a suitable period of time prior to the actual transplantation procedure. Preferably, the transfusion with donor specific irradiated blood is performed more than once and at least one week prior to transplantation of the organ or tissue. Presently it is preferred that the subject receive transfusion three times: at three weeks, at two weeks and at one week prior to the transplant. After the subject has received transfusions of suitably irradiated donor specific blood, the organ or tissues is transplanted into the subject using conventional surgical procedures.

An alternative approach to the use of transfused, irradiated donor specific blood to enhance the acceptance of transplanted, foreign organs or tissues involves the use of irradiated foreign organs or tissues. Accordingly, this invention also provides a method for enhancing acceptance of transplanted foreign organs or tissues in a subject which comprises treating the foreign organ or tissue to be transplanted with a suitable dose of ultraviolet radiation for an appropriate period of time and then transplanting the irradiated foreign organ or tissue into the subject.

Once again the method is applicable to a wide variety of subjects, the primary use presently contemplated being human patients requiring transplant surgery, e.g., a replacement kidney, heart, lung, liver or intestine or replacement tissue derived from such organs or from other body tissues, e.g., pancreatic islet cells or bone marrow.

Although varying dosages of ultraviolet radiation may be employed for differing periods of time the presently preferred dose is one whose intensity is less than about 1000 J/m$^2$ and to which the subject is exposed for at least ten minutes, e.g., twenty minutes. The irradiated organ or tissue may then be transplanted into the subject. The time within which the implant surgery is performed may vary as may the time during which the irradiated organ or tissue is stored prior to use, the limits depending primarily upon the nature of the organ or tissue. Generally, the irradiated organ or tissue will be employed within a few days after irradiation, e.g., within 24 hours after irradiation. The actual transplantation is performed using conventional procedures.

EXPERIMENTAL DETAILS

A. UV-irradiated Donor Specific Blood

The following experiment relating to transfusion with irradiated donor specific blood is also set forth in the Aug. 19, 1983 issue of Science, volume 221, pages 754–756.

The successful transplantation of allogeneic pancreatic islets in mice depleted of cells bearing I region-associated antigens (Ia) by antiserum to Ia and the enhancement of skin allografts with this antiserum (1) suggest that allografted tissue depleted of Ia-bearing cells is accepted without being recognized as foreign. The type of Ia-bearing cell eliminated in such experiments is not known, but appears to be the dendritic cell; Ia-bearing dendritic cells are present in frozen tissue sections of islets and in the parenchyma of human kidneys, hearts, thyroid glands, and skin (2). Such a wide distribution suggests that the depletion of Ia-bearing cells from organ allografts may have clinical applicability not only to pancreatic islet transplantation but to transplantation of other organs as well. Although abolition of the initial recognition of a foreign allograft by the host is critical to successful allografting without further immunosuppression, maintenance of a functioning allograft may depend on the initiation of donor-specific suppressor T lymphocytes in the host (3). Such a state of unresponsiveness to allogeneic tissue is seen when Ia-negative platelets and red blood cells are unable to provoke a primary immune response and attenuate the subsequent challenge with Ia-bearing cells (3).

This idea was further supported when treatment of diabetic mice with donor blood depleted of Ia-bearing cells allowed successful transplantation of fresh, untreated allogeneic islets of the blood donor strain (4). It appears, therefore, that immunization with Ia-negative donor blood cells induces immunological unresponsiveness to the donor strain in recipients by the stimulation of specific suppressor cells.

Our demonstration of a rapid and simple method of inducing donor-specific immunological unresponsiveness in adult animals that allows long-term survival of islet allografts is consistent with recent clinical studies in which donor-specific transfusions led to 1-year survival of kidney allografts in more than 90 percent of mismatched donor-recipient pairs of one haplotype (5). Since ultraviolet (UV) irradiation of the stimulating cell population in a primary mixed-lymphocyte reaction (MLR) leads to little or no proliferative response (6), we hypothesized that Ia-bearing cells may not need to be eliminated from blood before its use for immunization, but may need to be inactivated with UV light, leading to abrogation of the stimulating allogeneic signal while leaving major histocompatibility complex antigens intact for the induction of donor-specific immunological unresponsiveness.

Rats of strain ACI (RT1$^a$) were made diabetic with intravenous streptozotocin (60 mg/kg). A rat was used as a recipient of blood and islets only if its blood glucose concentration exceeded 300 mg/dl for more than 3 weeks. Islet allografts were considered to have been rejected when plasma glucose was greater than 200 mg/dl on two successive daily measurements.

Whole blood was obtained from normal Lewis rats (RT1$^l$) by intracardiac puncture. The blood was diluted 1:50 in phosphate-buffered saline (PBS), placed with a magnetic stirring bar into 250-ml petri dishes, and irradiated for 20 minutes with two FS-20 lamps located 10 cm from the dishes. The blood cells were then centrifuged and the resulting pellet was resuspended in PBS to 50 percent packed cell volume. Each diabetic ACI rat received 1 ml of UV-irradiated blood or 1 ml of identically treated non-irradiated blood adjusted to 50 percent packed cell volume through the penile vein 3 weeks, 2 weeks, and 1 week before islet transplantation. One group of diabetic ACI rats received islets without previous transfusions.

Pancreatic islets were harvested from Lewis (RT1$^l$) and Wistar Furth (WF) (RT1$^u$) rats by the collagenase technique (7) and Ficoll gradient separation (8), with subsequent handpicking under a dissecting microscope. Some 1200 to 1500 freshly prepared allogeneic islets were transplanted intraportally into four groups of diabetic ACI rats. Two groups of islet recipients (groups 1 and 4) were first transfused with UV-irradiated whole blood. One control group (group 3) was not transfused before receiving islets, while a second control group (group 2) was transfused with nonirradiated blood before allografting.

In vitro studies of Lewis rat peripheral blood lymphocytes that were either non-irradiated or irradiated in a manner identical to that of the whole blood were performed in conjunction with the above study (9). The binding of monoclonal antibodies to rat Ia (MRC-OX4) (10) and of a polyclonal rabbit antiserum to rat lymphocytes (M.A. Bioproducts) was determined with $^{125}$I-labeled staphylococcal protein A on Lewis rat lymphocytes obtained from peripheral blood that was UV-irradiated or untreated with irradiation (11). MLR's were performed by using Lewis lymphocytes obtained from irradiated or untreated whole blood (identical treatment to that described for transfusions before islet allografting) as stimulator cells and ACI thoracic duct lymphocytes as responders (12).

Lewis peripheral blood lymphocytes obtained from UV-irradiated blood did not stimulate ACI thoracic duct lymphocytes significantly compared to Lewis lympoocytes obtained from nonirradiated whole blood (Table 1).

TABLE 1

Effect of UV irradiation on the stimulatory activity of Lewis rat peripheral blood lymphocytes (PBL) in MLR's. Values are means ± standard deviations.

| Responder | Stimulator | [$^3$H]thymidine incorporation (count/min) |
|---|---|---|
| ACI | ACI | 465 ± 153 |
| ACI | Lewis PBL | 5371 ± 543 |
| ACI | Lewis PBL and UV irradiation for 20 minutes | 722 ± 102 |

In the radioimmunoassay there appeared to be no significant difference between lymphocytes obtained from irradiated Lewis peripheral blood and untreated blood (Table 2).

TABLE 2

Effect of UV light on the serological reactivity of Lewis rat PBL surface antigens. Values are mean counts (± standard deviations) of $^{125}$I-labeled staphylococcal protein A bound per assay (background, 200 count/min).

| Antigen | PBL | PBL and UV irradiation (20 minutes) |
|---|---|---|
| Rabbit antiserum to rat lymphocytes | 2996 ± 172 | 3315 ± 434 |
| Monoclonal antibodies to rat Ia (MRC/OX4) | 2050 ± 421 | 1963 ± 268 |

The rabbit antiserum to rat lymphocytes and the monoclonal antibody to rat Ia (MRC/OX4) showed similar binding to Lewis peripheral blood lymphocytes, regardless of whether UV irradiation was used. Therefore we did not detect allostimulation in the MLR's by peripheral blood lymphocytes that were irradiated, despite the clear demonstration by radioimmunoassay that major histocompatibility antigens are quantitatively unchanged by previous irradiation of lymphocytes.

Figure 1:
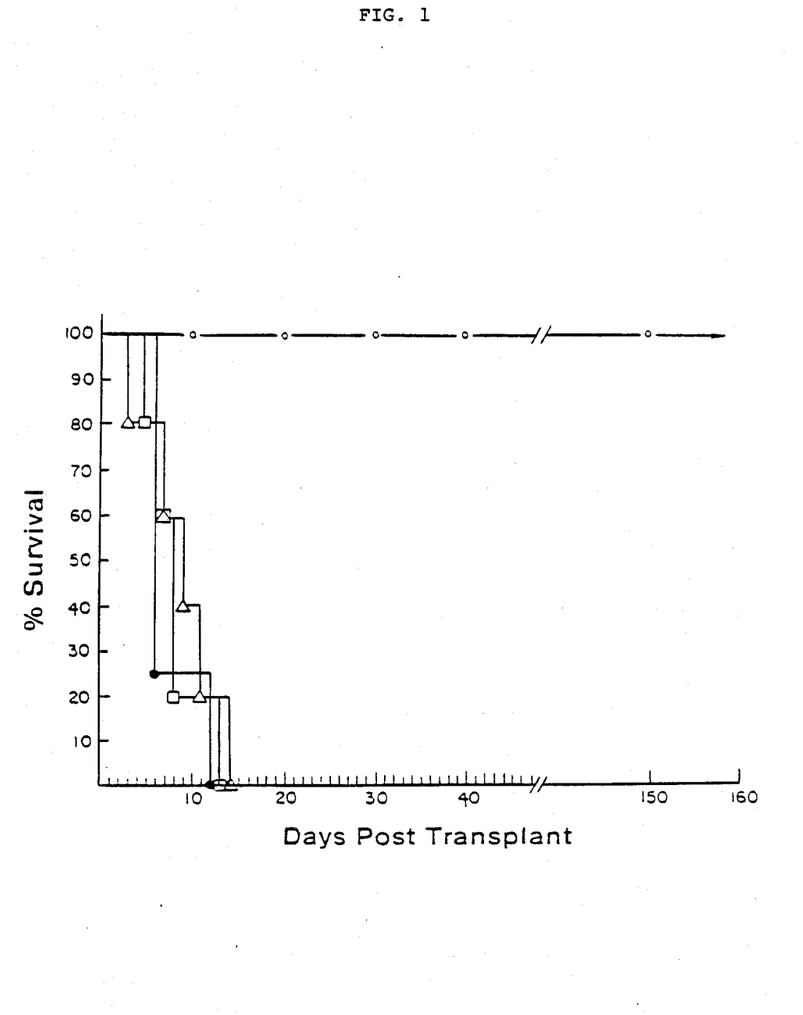
FIG. 1 Percentage of graft survival in ACI diabetic recipients of islet allografts. Group I (O) transfused Lew UV irradiated blood and Lew islet allografts, Group II (Δ) transfused non-treated Lew blood and Lew islet allografts, Group III (□) control recepients without transfusion and Lew islet allografts, and Group IV (•) transfused as in Group I but transplanted third-party W/F (RTl$^u$) islets.

In the in vivo allograft experiments, diabetic ACI recipients that were transfused with UV-irradiated Lewis whole blood and subsequently transplanted with fresh Lewis islets (group 1) showed 100 percent conversion to normoglycemia. There was no tissue rejection in any of the ten animals in a period of more than 160 days after allografting. The nontransfused control group (group 3) and the control group transfused with nonirradiated blood (group (2) had similar mean survival times (8.2±2.9 and 8.8±4.1 days, respectively. When third-party islets were transplanted into diabetic ACI recipients transfused previously with irradiated Lewis whole blood (group 4), rejection of islets and return to the diabetic state occurred in a normal fashion (mean survival time, 7.5±3.0 days) (Table 3 and FIG. 1).

TABLE 3

Survival of islet transplants in the various treatment and control groups.

| Group | Treatment | Donor strain | N | Survival time (days) | Mean survival time ± standard deviation (days) |
|---|---|---|---|---|---|
| 1 | Irradiated Lewis blood | Lewis | 10 | >160 | |
| 2 | Lewis blood | Lewis | 5 | 3, 7, 9, 11, 14 | 8.8 ± 4.1 |
| 3 | None | Lewis | 5 | 5, 7, 8, 8, 13 | 8.2 ± 2.9 |
| 4 | Same as group 1 | WF | 4 | 6, 6, 6, 12 | 7.5 ± 3.0 |

These results demonstrate that transfusions of UV-irradiated whole blood of the donor type lead to a prolonged and perhaps indefinite survival of islet allografts and induction of normoglycemia in the diabetic host. These results are obtained without any immunosuppressive drugs, and the induction of unresponsiveness with UV-irradiated blood appears to be donor-specific. Parallel in vitro studies suggest that UV irradiation of blood abrogates the allostimulatory effect of blood lymphocytes in the MLR even in the presence of UV-absorbing red blood cells while not affecting the serological reactivity of Ia (as shown by radioimmunoassay) or antigens detected by rabbit antiserum to rat lymphocytes. These findings suggest that allostimulation requires the presence of a metabolically active Ia-bearing cell and that immunization with inactivated cells can lead to subsequent strain-specific immunological unresponsiveness to islet allografts in rats. Although immunological unresponsiveness to allografts and induction of T suppressor cells have been demonstrated with various blood transfusion protocols, the results were inconsistent and immunosuppression was generally required (13). We believe, as Faustman et al. (4) suggested, that in islet transplantation sensitization and subsequent rejection occurs because of "contaminating" Ia-bearing cells; however, our findings suggest that these cells need not be physically eliminated but may simply be inactivated to result in immunological unresponsiveness of the host without the need for further immunosuppressive intervention. Studies of recombinant mouse strains (14) support the conclusion that the Ia signal is altered by UV irradiation without a significant change in the class I antigens. This may occur through metabolic inactivation of the cell.

Thus, UV irradiation offers a promising method for the induction of donor-specific immunological unresponsiveness. The use of UV irradiation for immunological inactivation of blood products could be easily applicable to allotransplantation in other species for which specific antibodies to Ia are not available or required. This approach may prove useful in the transplantation of human organs, an area where donor-specific blood transfusions are already in use, and may eliminate the possibility of sensitization to major histocompatibility antigens of the donor. Prolonged (or indefinite) islet allograft survival and correction of diabetes may be achieved by this simple maneuver without requiring immunosuppression of the diabetic host.

B. UV-irradiated Organs and Tissues

Although major histocompatibility complex (MHC) disparity causes rejection of grafted tissue, the recognition by the host of this incompatibility appears to be the critical factor in initiating the rejection process. The recognition of foreignness by the host appears to require both the pressence of Class I and Class II MHC antigens on the graft and lympho-reticular cells bearing both classes of antigens are thought to be responsible for sensitizing the host toward a primary immune response (15-17). We present data that ultraviolet (UVB) irradiation, at an appropriate dose which can abrogate an MLC response after irradiation of rat dendritic stimulator cells (18-21), can also attenuate the immunogenicity of pancreatic islets without alteration of its endocrine function and prolong rat islet allograft survival in diabetic hosts without the use of immunosuppressive agents.

The exact nature of the 'passenger leukocyte' which has been implicated in causing graft rejection is not clear.

Figure 2:
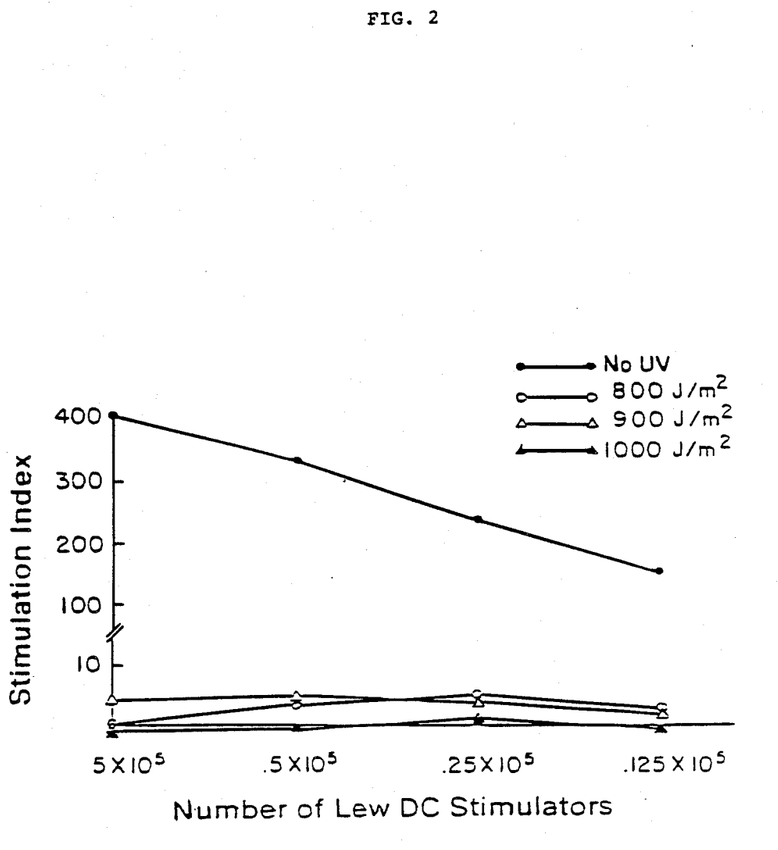

The rat dendritic cells have been demonstrated to be extremely powerful as accessory cells in T cell proliferation and in causing acute rejection of otherwise 'passenger leukocyte'-depleted rat kidneys (22). We first investigated the ability of UV irradiation of rat dendritic cells, derived from afferent lymph, to attenuate their stimulatory activity in an MLC. Using ACI (RTl$^a$) rat thoracic duct lymphocytes (TDL) as responders and Lew (RT1$^1$) rat dendritic cells (DC) as stimulators, a high stimulation index (SI) of >400 was obtained with 10$^5$ DC (FIG. 2). When the number of DC stimulators were decreased to 125×10$^5$ the SI remained markedly elevated (162).

Dendritic cells, UV irradiated (FS-20 at exposures of 800 J/m$^2$ to 1000 J/m$^2$) were completely ineffective as stimulators in the MLC with resulting SI of 3. Although dendritic cells are extremely powerful allogeneic stimulators as demonstrated in the MLC (20, 23) and in causing graft rejection (21), they appear to be inactivated by UV irradiation but not by gamma irradiation.

Figure 3:
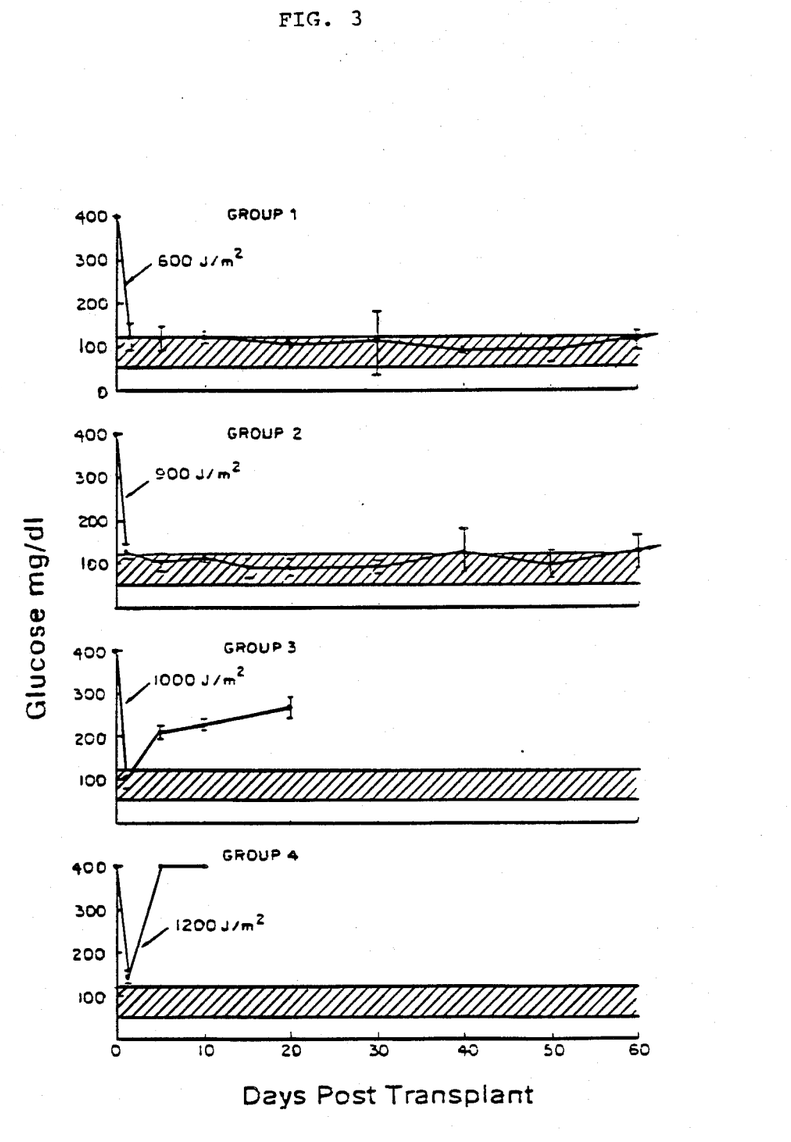

Once the dose range of UV irradiation necessary to attenuate the MLC response was defined, we exxamined the ability of UV irradiated islets (same dose range) to reverse the diabetic state in syngeneic streptozotocin (STZ)-induced diabetic rats (FIG. 3). Lewis rat islets irradiated with 1000 J/m$^2$ and subsequently transplanted intraportally into diabetic Lewis recipients converted diabetic animals to a normoglycemic state for less than 5 days; islets irradiated with 1100 or 1200 J/m$^2$ failed to convert them. Irradiation (UV) with 600 or 900 J/m$^2$ resulted in indefinite conversion to normoglycemia in all diabetic syngeneic recipients. Thus, the UV irradiation dose that can abrogate the proliferative response in the MLC using 10$^5$ DC as stimulators, has no deleterious effect on the in vivo endocrine function of syngeneic islet grafts irradiated with 900 J/m$^2$.

Figure 4:
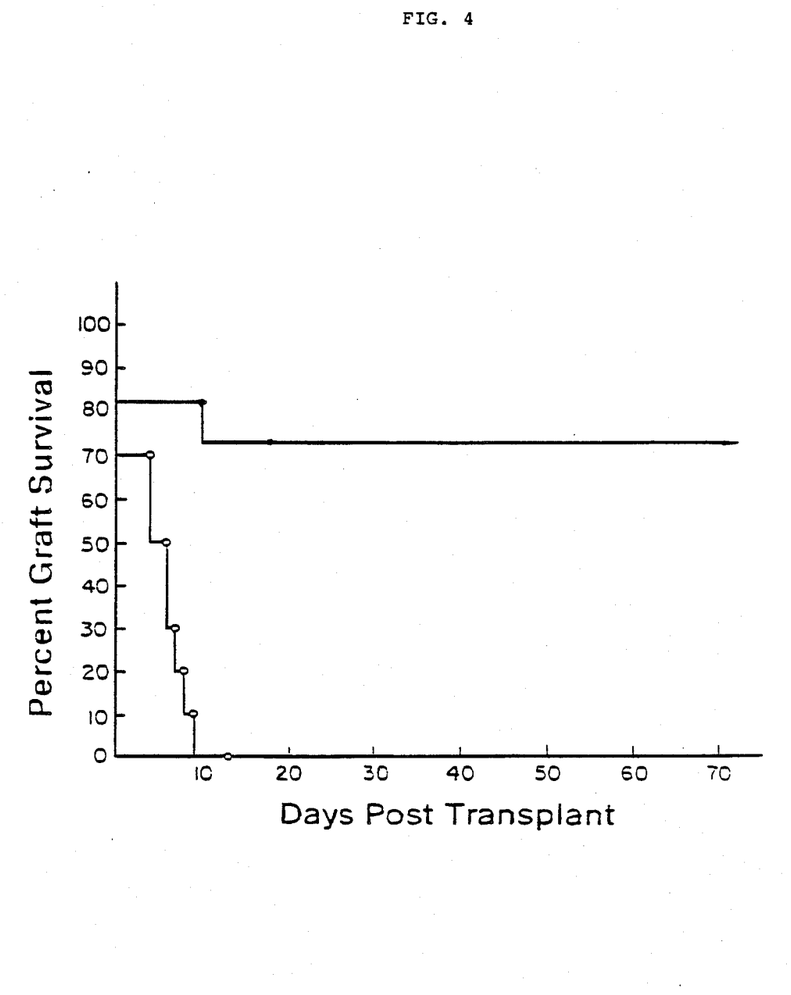
FIG. 4. Survival of Lewis UV irradiated and non-irradiated islets in diabetic ACI recipients. ACI rats were made diabetic with i.v. streptozotocin as described before. Lewis islets were isolated as described for syngeneic transplants and were UV irradiated with 900 J/m$^2$ exactly as described previously. UV and non-UV irradiated islets were cultured for 24 hours prior to intraportal transplantation. Rejection of islets was considered to have occurred if blood glucose was 200 mg/dl on two consecutive daily measurements. — Lewis islets to ACI with UV irradiation; — Lewis islets to ACI with prior UV irradiation.

To determine whether the immunogenicity of allogeneic islets was reduced after such irradiation, Lewis (RT1$^1$) islets were transplanted into STZ-induced diabetic AC1 rats (FIG. 4, Table 4).

TABLE 4

The Effect of Direct UV Irradiation on Lewis Islet Allograft Survival in Diabetic ACI Recipients

| Islet Treatment | n | Survival Time (Days) | MST ± SD |
|---|---|---|---|
| 24 hour culture | 10 | 4, 4, 4, 6, 6, 7, 7, 8, 9, 13 | 6.8 ± 2.7 days |
| UV & 24 hour culture | 11 | 10, 10, 18, 75, 75, 75, 75, 110, 110, 110, 110 | >80 days |

All the control ACI animals receiving Lewis islets cultured for 24 hours at 37° C. rejected their grafts and became diabetic again at 6.8±2.7 days. When Lewis islets were exposed to 900 J/m$^2$ of UV irradiation, cultured for 24 hours and then transplanted into diabetic ACI recipients, islet survival was prolonged in 8 of 11 transplanted animals to more than 70 days (4>110 days) with all 8 still normoglycemic. These results indicate that treatment of allogeneic rat islets with UV irradiation prior to allotransplantation, at an exposure that is not deleterious to its endocrine function, can reduce the islets' immunogenicity and permits prolonged allograft survival without immunosuppression.

The importance of passenger leukocytes in initiating allograft rejection has been a recurring theme in transplantation-immunology (24-27). In the transplantation of islets various in vitro culture techniques (28, 29) have been used to prolong allograft survival, all relying on the presumption that long-term cultures selectively deplete the islet of lympho-reticular elements (30). More recently, the use of anti-Class II MHC antigen sera and complement to remove Ia bearing cells have permitted prolonged allogeneic islet graft survival in the mouse (31). The exact nature of passenger leukocytes involved is uncertain. This question has been recently approached by studies of the role of interstitial dendritic cells in the primary alloactivation of T cells in MLC and their role in the rejection of rat kidney allografts (20, 22, 32). The ubiquitous presence of such Class II MHC antigen bearing cells identified in rat islets, kidneys and hearts would suggest that these cells may be the putative 'passenger leukocytes' responsible for direct sensitization of the host toward the allograft antigen (21, 33). In this study, we have demonstrated that dendritic cells are extremely powerful activators of relevant T responder cells in the primary MLC, and that their stimulatory activity can be completely inactivated with appropriate UV irradiation.

Many previous studies have shown that UV irradiation has a selective effect on antigen presenting cells (APC) (34-36) and that passive transfer of UV irradiated APC can induce antigen specific T suppressor cells (37). These and other studies (38-40) would therefore suggest that improper antigen presentation, i.e., allograft without stimulatory leukocytes may induce preferentially production of T suppressor cells or effect nonrecognition of foreignness until antigens are represented to host T cells by host APC's whereby production of donor-specific T suppressor cells may also occur. We have previously shown that UV irradiation of peripheral blood lymphocytes does not quantitatively alter cell surface antigens including Class II MHC antigens (41). It would appear that primary allostimulation not only requires Class I and Class II antigen bearing lympho-reticular cells (31, 42), but that they must be metabolically active and are susceptible to inactivation by UV irradiation (43).

The prolonged survival of irradiated islets suggests that their exposure to UV irradiation that is effective in abrogating the MLC response, is selectively effective in attenuating the stimulatory activity of the interstitial dendritic cells or other allostimulatory cells present in the islet preparation. Since islets are not single cell suspensions, some allostimulatory leukocytes may escape complete inactivation which might explain a 27% failure rate in prolongation of islet allograft survival. A more precise quantitative method of delivery of UV irradiation and elucidation of its ultimate effect on islet function and simultaneously on the allostimulatory activity of the dendritic and other lympho-reticular cells contained in the islet preparation, is necessary before this approach is uniformly successful.

In conclusion, we have demonstrated that brief UV irradiation of islets can reduce their immunogenicity without affecting their endocrine function and permit longterm islet allograft survival and function in diabetic hosts without the use of any immunosuppressive agents. This approach offers distinct advantages over long-term culture techniques and does not require the use of specific anti-Class II MHC antigen sera. We believe that this study forms the basis for islet transplantation in other animals and ultimately in man.

REFERENCES AND NOTES

1. D. Faustman, V. Hauptfield, P. E. Lacy, J. M. Davie, Proc. Natl. Acad. Sci. U.S.A. 78, 5156 (1981); N. A. Staines, K. Guy, D. A. L. Davies, Eur. J. Immunol. 5, 782 (1975).
2. A. Rabinovitch, R. Alejandro, J. Noel, J. P. Brunschwig, U.S. Ryan, Diabetes 31 (Suppl. 4), 48 (1982); D. N. J. Hart and J. W. Fabre, J. Exp. Med. 153, 347 (1981); S. V. Fuggle et al., Transplantation 35, 385, (1983).
3. K. I. Welsh, H. Burgos, J. R. Batchelor, Eur. J. Immunol. 7, 267 (1977); P. B. Medawar, in *Biological Problems of Grafting*, F. Albert and G. Lejeune-Ledant, Eds. (Blackwell, Oxford, 1959), p. 8.
4. D. Faustman, P. Lacy, J. Davie, V. Hauptfeld, Science 217, 157 (1982).
5. O. Salvatierra, F. Vincenti, W. Amend, Ann. Surg. 192, 543 (1980).
6. P. Hayry and L. C. Andersson, Scand. J. Immunol. 5, 391 (1976); K. Lindahl-Kiessling and J. Safwenberg, Int. Arch. Allergy Appl. Immunol. 441, 670 (1971).
7. P. E. Lacy and M. Kostianovsky, Diabetes 16, 35 (1967).
8. A. M. Lindall, M. Steffess, R. Sorenson, Endocrinology 85, 218 (1969).
9. A. Boyum, Scand. J. Clin. Lab. Invest. 21 (Suppl. 97), 77, (1968).
10. W. R. McMaster and A. F. Williams, Eur. J. Immunol. 9, 426 (1979).
11. J. P. Brown, J. D. Jamerius, I, Hellstrom, J. Immunol. Methods 31, 201 (1979); G. S. Eisenbarth, B. F. Haynes, J. A. Schroer, A. S. Fauci, J. Immunol. 124, 1237 (1980).
12. The MLR was conducted in 96-well U-bottom microtiter plates (Falcon Plastics) in RPMI 1640 medium supplemented with penicillin and streptomycin (100 mg/ml each), L-glutamine, and 10 percent rat serum. Thoracic duct lymphocytes from ACI ras were used as responders and peripheral blood lymphocytes (purified by Ficoll-Hypaque sedimentation) from ultraviolet-irradiated or untreated blood were used as stimulators at $5 \times 10^5$ cells per well. Plates were harvested after 96 hours with a 16-hour exposure to thymidine.
13. P. Terasaki, Transplant. Proc. 14, 1 (1982); J. W. Fabre and P. J. Morris, Transplantation 14, 608 (1972); H. Okazaki, T. Maki, M. L. Wood, ibid. 129, 341 (1980); L. Brent, T. Horsburgh, P. J. Wood, Transplant. Proc. 12, 464 (1980).
14. F. H. Bach et al., Immunol. Rev. 35, 76 (1977); B. J. Alter, D. J. Schendel, F. H. Bach, J. Exp. Med. 137, 1303 (1973).
15. D. W. Talmage, G. Dart, J. Radovich, K. J. Lafferty, Science 191, 385 (1976).
16. K. J. Lafferty, J. Woolnough, Immunological Rev. 53, 231 (1977).
17. G. Snell, Ann. Rev. Microbiol. 2, 439 (1957).
18. P. Hayry, L. C. Andersson, Scand. J. Immunol. 5, 391 (1976).
19. K. Lindahl-Kiessling, J. Safwenberg, Int. Arch. Allergy 41, 670 (1971).
20. D. W. Mason, C. W. Pugh, M. Webb, Immunology 44, 75 (1981).
21. W. E. F. Klinlert, J. H. LaBadie, W. E. Bowers, J. Exp. Med., 156, 1 (1982).
22. R. I. Lechler, J. R. Batchelor, J. Exp. Med. 155, 34 (1982).
23. R. M. Steinman, M. D. Witmer, Proc. Natl. Acad. Sci. USA 75, 5132 (1978).
24. K. J. Lafferty, S. J. Prowse, M. Agostino, C. J. Simenovic, Transplant Proc. 15, 1366 (1983).
25. S. J. Prowse, K. J. Lafferty, C. J. Simenovic, M. Agostino, K. M. Bowen, E. J. Steele, Diabetes, 31, 30(1982).
26. R. E. Billingham, Cell. Immunol., 2, 1 (1971).
27. W. K. Silvers, H. L. Fleming, A. Naji, C. F. Barker, Diabetes 31, 60 (1982).
28. P. E. Lacy, J. M. Davie, E. H. Finke, Science 204, 312 (1979).
29. M. Kedinger, K. Haffen, R. Grenier, R. Eloy, Nature 270, 736 (1977).
30. A. Rabinovitch, R. Alejandro, J. Noel, J. P. Brunschweig, U.S. Ryan, Diabetes, 31, 48 (1982).
31. D. Faustman, V. Hauptfeld, P. E. Lacy, J. Davie, Proc. Natl. Acad. Sci. USA 78, 5156 (1981).
32. R. M. Steinman, B. Gutchinov, M. Witmer, M. C. Nussensweig, J. Exp. Med. 157, 613 (1983).
33. D. N. J. Hart, J. W. Fabre, J. Exp. Med. 153, 347 (1981).
34. L. J. Fox, L. L. Perry, S. Man Sun, B. Benacenaf, M. I. Greene, Clin. Immunol. & Immunopath. 17, 141 (1980).
35. N. L. Letvin, M. I. Greene, B. Benacenaf, R. N. Germain, Proc. Natl. Acad. Sci. USA 77, 3882 (1980).
36. I. J. Fox, S. Man Fun, B. Benacenaf, M. I. Greene, Transplantation 31, 262 (1981).
37. M. I. Greene, S. Man Sun, M. Kripke, B. Benacenaf, Proc. Natl. Acad. Sci. USA 76, 6591 (1979).
38. I. M. Zitron, J. Ono, P. E. Lacy, J. M. Davie, Transplantation 32, 156 (1981).
39. C. G. Janney, J. M. Davie, P. E. Lacy, E. H. Finke, Transplantation 33, 585 (1982).
40. K. I. Welsh, H. Burgos, J. R. Batchelor, Eur. J. Immunol., 7, 267 (1977).
41. H. T. Lau, K. Reemtsma, M. A. Hardy, Science, 221, 754 (1983).
42. D. Davies, N. Staines, Transplant Rev. 30, 18 (1976).

43. D. W. Talmage, J. A. Woolnough, H. Hemmingson, L. Lopez, K. J. Lafferty, Proc. Natl. Acad. Sci. USA 75, 4610 (1977).
44. R. M. Steinman, Z. A. Cohn, J. Exp. Med., 139, 380 (1974).
45. R. M. Steinman, M. L. Nussensweig, Immunological Rev., 55, 127 (1980).
46. P. E. Lacy, M. A. Kostianovsky, Diabetes 16, 35 (1972).
47. A. Lindall, M. Steffes, R. Sorenson, Endocrinology 84, 218 (1969).

What is claimed is:

1. A method for transplanting a foreign organ or tissue from a donor into a subject so as to enhance acceptance of the transplanted foreign organ or tissue by the subject which comprises removing the foreign organ or tissue from the donor, irradiating the removed foreign organ or tissue to be transplanted with ultraviolet —B radiation at a dosage of less than 1000 $J/m^2$ so as to enhance acceptance of the transplanted foreign organ or tissue and then transplanting the irradiated foreign organ or tissue into the subject.

2. A method according to claim 1, wherein the subject is a human being.

3. A method according to claim 1, wherein the organ or tissue to be transplanted is or is derived from kidney, heart, lung, liver, intestine or bone marrow.

4. A method according to claim 1, wherein the organs or tissues are pancreatic islet cells.

5. A method according to claim 1, wherein the irradiation is effected for a period of time greater than about ten minutes.

* * * * *